United States Patent
Gefen

(10) Patent No.: US 9,370,417 B2
(45) Date of Patent: Jun. 21, 2016

(54) FOVEATED RETINAL PROSTHESIS

(71) Applicant: Nano-Retina, Inc., Wilmington (DE)

(72) Inventor: Ra'anan Gefen, Re'ut (IL)

(73) Assignee: NANO-RETINA, INC., Wilmington, DE (US)

( * ) Notice: Subject to any disclaimer, the term of this patent is extended or adjusted under 35 U.S.C. 154(b) by 418 days.

(21) Appl. No.: 13/827,919

(22) Filed: Mar. 14, 2013

(65) Prior Publication Data
US 2014/0277435 A1    Sep. 18, 2014

(51) Int. Cl.
*A61F 2/16* (2006.01)
*A61N 1/05* (2006.01)
*A61N 1/36* (2006.01)

(52) U.S. Cl.
CPC ............ *A61F 2/1624* (2013.01); *A61N 1/0543* (2013.01); *A61N 1/36046* (2013.01)

(58) Field of Classification Search
CPC ............ A61N 1/0543; A61N 1/36046; A61N 1/3787; A61N 1/0622; A61N 1/04; A61N 1/05; A61N 1/0553; A61N 1/36; A61N 1/36125; A61N 2005/0647; A61F 9/08; A61F 2/14; A61F 9/0017; A61F 2250/0001; A61F 9/00727; A61B 2560/0219; A61B 2560/0214; A61B 2562/02; A61B 2562/0209; A61B 2562/0233; A61B 2562/0238; A61B 2562/164; A61B 5/00; A61B 5/0059; A61B 5/04001; A61B 5/6814; H01L 27/14627; G02C 11/10
See application file for complete search history.

(56) References Cited

U.S. PATENT DOCUMENTS

| | | | |
|---|---|---|---|
| 1,662,446 A | 3/1928 | Wappler |
| 2,721,316 A | 10/1955 | Shaw |
| 2,760,483 A | 8/1956 | Tassicker |
| 4,197,850 A | 4/1980 | Schulman et al. |
| 4,262,294 A | 4/1981 | Hara et al. |
| 4,272,910 A | 6/1981 | Danz |
| 4,324,252 A | 4/1982 | Rossing et al. |
| 4,486,861 A | 12/1984 | Harmel |
| 4,551,149 A | 11/1985 | Sciarra |
| 4,601,545 A | 7/1986 | Kern |

(Continued)

FOREIGN PATENT DOCUMENTS

| | | |
|---|---|---|
| CA | 2235216 | 4/1997 |
| CN | 2650300 | 10/2004 |

(Continued)

OTHER PUBLICATIONS

Official Action dated Oct. 22, 2013, which issued during the prosecution of Applicant's U.S. Appl. No. 13/148,461.

(Continued)

*Primary Examiner* — Deborah Malamud
(74) *Attorney, Agent, or Firm* — Sughrue Mion, PLLC

(57) ABSTRACT

Apparatus is provided having an intraocular device for implantation entirely in a subject's eye, the intraocular device including: a photosensor array having a plurality of photosensors, each photosensor detects ambient photons and generates a signal in response thereto. A spatial density of the photosensors in a central portion of the array is greater than a spatial density of the photosensors in an outer portion of the array. The intraocular device additionally includes a plurality of stimulating electrodes and driving circuitry coupled to the photosensors, and configured to drive the electrodes to apply electrical pulses to a retina of the eye in response to the signals from the photosensors. Other applications are also described.

6 Claims, 9 Drawing Sheets

(56) References Cited

U.S. PATENT DOCUMENTS

| | | |
|---|---|---|
| 4,628,933 A | 12/1986 | Michelson |
| 4,664,117 A | 5/1987 | Beck |
| 4,786,818 A | 11/1988 | Mead et al. |
| 4,837,049 A | 6/1989 | Byers et al. |
| 4,903,702 A | 2/1990 | Putz |
| 4,914,738 A | 4/1990 | Oda et al. |
| 4,969,468 A | 11/1990 | Byers et al. |
| 5,016,633 A | 5/1991 | Chow |
| 5,024,223 A | 6/1991 | Chow |
| 5,081,378 A | 1/1992 | Watanabe |
| 5,108,427 A | 4/1992 | Majercik et al. |
| 5,109,844 A | 5/1992 | de Juan, Jr. et al. |
| 5,133,356 A | 7/1992 | Bryan et al. |
| 5,147,284 A | 9/1992 | Fedorov et al. |
| 5,159,927 A | 11/1992 | Schmid |
| 5,215,088 A | 6/1993 | Normann et al. |
| 5,313,642 A | 5/1994 | Seigel |
| 5,314,458 A | 5/1994 | Najafi et al. |
| 5,397,350 A | 3/1995 | Chow et al. |
| 5,411,540 A | 5/1995 | Edell et al. |
| 5,476,494 A | 12/1995 | Edell et al. |
| 5,526,423 A | 6/1996 | Ohuchi et al. |
| 5,556,423 A | 9/1996 | Chow et al. |
| 5,575,813 A | 11/1996 | Edell et al. |
| 5,597,381 A | 1/1997 | Rizzo, III |
| 5,608,204 A | 3/1997 | Hofflinger et al. |
| 5,665,954 A | 9/1997 | Bard et al. |
| 5,674,263 A | 10/1997 | Yamamoto et al. |
| 5,735,882 A | 4/1998 | Rottenberg et al. |
| 5,769,875 A | 6/1998 | Peckham et al. |
| 5,800,478 A | 9/1998 | Chen et al. |
| 5,800,533 A | 9/1998 | Eggleston et al. |
| 5,800,535 A | 9/1998 | Howard, III |
| 5,835,250 A | 11/1998 | Kanesaka |
| 5,836,996 A | 11/1998 | Doorish |
| 5,837,995 A | 11/1998 | Chow et al. |
| 5,850,514 A | 12/1998 | Gonda et al. |
| 5,865,839 A | 2/1999 | Doorish |
| 5,873,901 A | 2/1999 | Wu et al. |
| 5,895,415 A | 4/1999 | Chow et al. |
| 5,935,155 A | 8/1999 | Humayun et al. |
| 5,944,747 A | 8/1999 | Greenberg et al. |
| 5,949,064 A | 9/1999 | Chow et al. |
| 6,020,593 A | 2/2000 | Chow et al. |
| 6,032,062 A | 2/2000 | Nisch |
| 6,035,236 A | 3/2000 | Jarding et al. |
| 6,043,437 A | 3/2000 | Schulman et al. |
| 6,069,365 A | 5/2000 | Chow et al. |
| 6,075,251 A | 6/2000 | Chow et al. |
| 6,201,234 B1 | 3/2001 | Chow et al. |
| 6,230,057 B1 | 5/2001 | Chow et al. |
| 6,259,937 B1 | 7/2001 | Schulman et al. |
| 6,287,372 B1 | 9/2001 | Briand et al. |
| 6,298,270 B1 | 10/2001 | Nisch et al. |
| 6,324,429 B1 | 11/2001 | Shire et al. |
| 6,347,250 B1 | 2/2002 | Nisch et al. |
| 6,368,349 B1 | 4/2002 | Wyatt et al. |
| 6,389,317 B1 | 5/2002 | Chow et al. |
| 6,400,989 B1 | 6/2002 | Eckmiller |
| 6,427,087 B1 | 7/2002 | Chow et al. |
| 6,442,431 B1 | 8/2002 | Veraart et al. |
| 6,450,816 B1 | 9/2002 | Gerber |
| 6,458,157 B1 | 10/2002 | Suaning |
| 6,472,122 B1 | 10/2002 | Schulman et al. |
| 6,473,365 B2 | 10/2002 | Joh et al. |
| 6,498,043 B1 | 12/2002 | Schulman et al. |
| 6,507,758 B1 | 1/2003 | Greenberg et al. |
| 6,533,798 B2 | 3/2003 | Greenberg et al. |
| 6,574,022 B2 | 6/2003 | Chow et al. |
| 6,611,716 B2 | 8/2003 | Chow et al. |
| 6,647,297 B2 | 11/2003 | Scribner |
| 6,658,299 B1 | 12/2003 | Dobelle |
| 6,677,225 B1 | 1/2004 | Ellis et al. |
| 6,678,458 B2 | 1/2004 | Ellis et al. |
| 6,683,645 B1 | 1/2004 | Collins et al. |
| 6,738,672 B2 | 5/2004 | Schulman et al. |
| 6,755,530 B1 | 6/2004 | Loftus et al. |
| 6,758,823 B2 | 7/2004 | Pasquale et al. |
| 6,761,724 B1 | 7/2004 | Zrenner et al. |
| 6,762,116 B1 | 7/2004 | Skidmore |
| 6,770,521 B2 | 8/2004 | Visokay et al. |
| 6,785,303 B1 | 8/2004 | Holzwarth et al. |
| 6,792,314 B2 | 9/2004 | Byers et al. |
| 6,804,560 B2 | 10/2004 | Nisch et al. |
| 6,821,154 B1 | 11/2004 | Canfield et al. |
| 6,844,023 B2 | 1/2005 | Schulman et al. |
| 6,847,847 B2 | 1/2005 | Nisch et al. |
| 6,888,571 B1 | 5/2005 | Koshizuka et al. |
| 6,904,239 B2 | 6/2005 | Chow et al. |
| 6,908,470 B2 | 6/2005 | Stieqlitz et al. |
| 6,923,669 B1 | 8/2005 | Tsui et al. |
| 6,935,897 B2 | 8/2005 | Canfield et al. |
| 6,949,763 B2 | 9/2005 | Ovadia et al. |
| 6,961,619 B2 | 11/2005 | Casey |
| 6,970,745 B2 | 11/2005 | Scribner |
| 6,974,533 B2 | 12/2005 | Zhou |
| 6,976,998 B2 | 12/2005 | Rizzo et al. |
| 6,990,377 B2 | 1/2006 | Gliner et al. |
| 7,001,608 B2 | 2/2006 | Fishman et al. |
| 7,003,354 B2 | 2/2006 | Chow et al. |
| 7,006,873 B2 | 2/2006 | Chow et al. |
| 7,025,619 B2 | 4/2006 | Tsui et al. |
| 7,027,874 B1 | 4/2006 | Sawan et al. |
| 7,031,776 B2 | 4/2006 | Chow et al. |
| 7,035,692 B1 | 4/2006 | Maghribi et al. |
| 7,037,943 B2 | 5/2006 | Peyman |
| 7,047,080 B2 | 5/2006 | Palanker et al. |
| 7,058,455 B2 | 6/2006 | Huie, Jr. et al. |
| 7,071,546 B2 | 7/2006 | Fey et al. |
| 7,079,881 B2 | 7/2006 | Schulman et al. |
| 7,081,630 B2 | 7/2006 | Saini et al. |
| 7,096,568 B1 | 8/2006 | Nilsen et al. |
| 7,103,416 B2 | 9/2006 | Ok et al. |
| 7,107,097 B2 | 9/2006 | Stern et al. |
| 7,127,286 B2 | 10/2006 | Mech et al. |
| 7,127,301 B1 | 10/2006 | Okandan et al. |
| 7,130,693 B1 | 10/2006 | Montalbo |
| 7,133,724 B2 | 11/2006 | Greenberg et al. |
| 7,139,612 B2 | 11/2006 | Chow et al. |
| 7,147,865 B2 | 12/2006 | Fishman et al. |
| 7,149,586 B2 | 12/2006 | Greenberg et al. |
| 7,158,834 B2 | 1/2007 | Paul, Jr. |
| 7,158,836 B2 | 1/2007 | Suzuki |
| 7,160,672 B2 | 1/2007 | Schulman et al. |
| 7,162,308 B2 | 1/2007 | O'Brien et al. |
| 7,177,697 B2 | 2/2007 | Eckmiller et al. |
| 7,190,051 B2 | 3/2007 | Mech et al. |
| 7,191,010 B2 | 3/2007 | Ohta et al. |
| 7,224,300 B2 | 5/2007 | Dai et al. |
| 7,224,301 B2 | 5/2007 | Dai et al. |
| 7,235,350 B2 | 6/2007 | Schulman et al. |
| 7,242,597 B2 | 7/2007 | Shodo |
| 7,244,027 B2 | 7/2007 | Sumiya |
| 7,248,928 B2 | 7/2007 | Yagi |
| 7,251,528 B2 | 7/2007 | Harold |
| 7,255,871 B2 | 8/2007 | Huie, Jr. et al. |
| 7,257,446 B2 | 8/2007 | Greenberg et al. |
| 7,263,403 B2 | 8/2007 | Greenberg et al. |
| 7,271,525 B2 | 9/2007 | Byers et al. |
| 7,272,447 B2 | 9/2007 | Stett et al. |
| 7,291,540 B2 | 11/2007 | Mech et al. |
| 7,295,872 B2 | 11/2007 | Kelly et al. |
| 7,302,598 B2 | 11/2007 | Suzuki et al. |
| 7,314,474 B1 | 1/2008 | Greenberg et al. |
| 7,321,796 B2 | 1/2008 | Fink et al. |
| 7,342,427 B1 | 3/2008 | Fensore et al. |
| 7,377,646 B2 | 5/2008 | Suzuki |
| 7,379,000 B2 | 5/2008 | Dal et al. |
| 7,388,288 B2 | 6/2008 | Solzbacher et al. |
| 7,400,021 B2 | 7/2008 | Wu et al. |
| 7,447,547 B2 | 11/2008 | Palanker |
| 7,447,548 B2 | 11/2008 | Eckmiller |
| 7,480,988 B2 | 1/2009 | Ok et al. |
| 7,481,912 B2 | 1/2009 | Stelzle et al. |

(56) References Cited

U.S. PATENT DOCUMENTS

| | | |
|---|---|---|
| 7,482,957 B2 | 1/2009 | Dai et al. |
| 7,483,751 B2 | 1/2009 | Greenberg et al. |
| 7,493,169 B2 | 2/2009 | Greenberg et al. |
| 7,499,754 B2 | 3/2009 | Greenberg et al. |
| 7,539,544 B2 | 5/2009 | Greenberg et al. |
| 7,555,328 B2 | 6/2009 | Schulman et al. |
| 7,556,621 B2 | 7/2009 | Palanker et al. |
| 7,565,202 B2 | 7/2009 | Greenberg et al. |
| 7,565,203 B2 | 7/2009 | Greenberg et al. |
| 7,571,004 B2 | 8/2009 | Roy et al. |
| 7,571,011 B2 | 8/2009 | Zhou et al. |
| 7,574,263 B2 | 8/2009 | Greenberg et al. |
| 7,610,098 B2 | 10/2009 | McLean |
| 7,622,702 B2 | 11/2009 | Wu et al. |
| 7,630,771 B2 | 12/2009 | Cauller |
| 7,631,424 B2 | 12/2009 | Greenberg et al. |
| 7,638,032 B2 | 12/2009 | Zhou et al. |
| 7,666,523 B2 | 2/2010 | Zhou |
| 7,676,274 B2 | 3/2010 | Hung et al. |
| 7,691,252 B2 | 4/2010 | Zhou et al. |
| 7,706,887 B2 | 4/2010 | Tai et al. |
| 7,706,893 B2 | 4/2010 | Hung et al. |
| 7,709,961 B2 | 5/2010 | Greenberg et al. |
| 7,725,191 B2 | 5/2010 | Greenberg et al. |
| 7,734,352 B2 | 6/2010 | Greenberg et al. |
| 7,738,962 B2 | 6/2010 | Greenberg et al. |
| 7,749,608 B2 | 7/2010 | Laude et al. |
| 7,750,076 B2 | 7/2010 | Laude et al. |
| 7,751,896 B2 | 7/2010 | Graf et al. |
| 7,765,009 B2 | 7/2010 | Greenberg et al. |
| 7,766,903 B2 | 8/2010 | Blumenkranz et al. |
| 7,776,197 B2 | 8/2010 | Zhou |
| 7,831,309 B1 | 11/2010 | Humayun et al. |
| 7,834,767 B2 | 11/2010 | Shodo |
| 7,835,798 B2 | 11/2010 | Greenberg et al. |
| 7,840,273 B2 | 11/2010 | Schmid |
| 7,846,285 B2 | 12/2010 | Zhou et al. |
| 7,853,330 B2 | 12/2010 | Bradley et al. |
| 7,871,707 B2 | 1/2011 | Laude et al. |
| 7,877,866 B1 | 2/2011 | Greenberg et al. |
| 7,881,799 B2 | 2/2011 | Greenberg et al. |
| 7,887,681 B2 | 2/2011 | Zhou |
| 7,894,909 B2 | 2/2011 | Greenberg et al. |
| 7,894,911 B2 | 2/2011 | Greenberg et al. |
| 7,904,148 B2 | 3/2011 | Greenberg et al. |
| 7,908,011 B2 | 3/2011 | McMahon et al. |
| 7,912,556 B2 | 3/2011 | Greenberg et al. |
| 7,914,842 B1 | 3/2011 | Greenberg et al. |
| 7,937,153 B2 | 5/2011 | Zhou et al. |
| 7,957,811 B2 | 6/2011 | Caspi et al. |
| 7,962,221 B2 | 6/2011 | Greenberg et al. |
| 7,979,134 B2 | 7/2011 | Chow et al. |
| 7,983,308 B1 | 7/2011 | Johnston et al. |
| 7,989,080 B2 | 8/2011 | Greenberg et al. |
| 8,000,804 B1 | 8/2011 | Wessendorf et al. |
| 8,010,202 B2 | 8/2011 | Shah et al. |
| 8,010,206 B2 | 8/2011 | Dai et al. |
| 8,014,868 B2 | 9/2011 | Greenberg et al. |
| 8,014,869 B2 | 9/2011 | Greenberg et al. |
| 8,014,878 B2 | 9/2011 | Greenberg et al. |
| 8,024,022 B2 | 9/2011 | Schulman et al. |
| 8,034,229 B2 | 10/2011 | Zhou et al. |
| 8,046,078 B2 | 10/2011 | Greenberg et al. |
| 8,060,211 B2 | 11/2011 | Greenberg et al. |
| 8,060,216 B2 | 11/2011 | Greenberg et al. |
| 8,068,913 B2 | 11/2011 | Greenberg et al. |
| 8,078,284 B2 | 12/2011 | Greenberg et al. |
| 8,090,447 B2 | 1/2012 | Tano et al. |
| 8,090,448 B2 | 1/2012 | Greenberg et al. |
| 8,103,352 B2 | 1/2012 | Fried et al. |
| 8,121,697 B2 | 2/2012 | Greenberg et al. |
| 8,131,375 B2 | 3/2012 | Greenberg et al. |
| 8,131,378 B2 | 3/2012 | Greenberg et al. |
| 8,145,322 B1 | 3/2012 | Yao et al. |
| 8,150,526 B2 | 4/2012 | Gross et al. |
| 8,150,534 B2 | 4/2012 | Greenberg et al. |
| 8,160,713 B2 | 4/2012 | Greenberg et al. |
| 8,165,680 B2 | 4/2012 | Greenberg et al. |
| 8,170,676 B2 | 5/2012 | Greenberg et al. |
| 8,170,682 B2 | 5/2012 | Greenberg et al. |
| 8,180,453 B2 | 5/2012 | Greenberg et al. |
| 8,180,454 B2 | 5/2012 | Greenberg et al. |
| 8,180,460 B2 | 5/2012 | Nevsmith et al. |
| 8,190,267 B2 | 5/2012 | Greenberg et al. |
| 8,195,266 B2 | 6/2012 | Whalen, III et al. |
| 8,197,539 B2 | 6/2012 | Nasiatka et al. |
| 8,239,034 B2 | 8/2012 | Greenberg et al. |
| 8,244,362 B2 | 8/2012 | Yonezawa |
| 8,359,083 B2 | 1/2013 | Clark et al. |
| 8,428,740 B2 | 4/2013 | Gefen et al. |
| 8,567,048 B2 | 10/2013 | Singh et al. |
| 2001/0011844 A1 | 8/2001 | Ernst et al. |
| 2002/0091421 A1 | 7/2002 | Greenberg et al. |
| 2002/0173889 A1 | 11/2002 | Odinak et al. |
| 2003/0023297 A1 | 1/2003 | Byers et al. |
| 2003/0032946 A1 | 2/2003 | Fishman et al. |
| 2003/0100823 A1 | 5/2003 | Kipke et al. |
| 2003/0110508 A1 | 6/2003 | Bridgelall |
| 2003/0132946 A1 | 7/2003 | Gold |
| 2003/0181957 A1 | 9/2003 | Greenberg et al. |
| 2003/0208248 A1 | 11/2003 | Carter et al. |
| 2004/0054407 A1 | 3/2004 | Tashiro et al. |
| 2004/0078064 A1 | 4/2004 | Suzuki |
| 2004/0080026 A1 | 4/2004 | Minamio et al. |
| 2004/0082981 A1 | 4/2004 | Chow et al. |
| 2004/0088026 A1 | 5/2004 | Chow et al. |
| 2004/0098067 A1 | 5/2004 | Ohta et al. |
| 2004/0181265 A1 | 9/2004 | Palanker et al. |
| 2004/0189940 A1 | 9/2004 | Kutschbach et al. |
| 2005/0015120 A1 | 1/2005 | Seibel et al. |
| 2005/0119605 A1 | 6/2005 | Sohn |
| 2005/0146954 A1 | 7/2005 | Win et al. |
| 2005/0168569 A1 | 8/2005 | Igarashi et al. |
| 2006/0106432 A1 | 5/2006 | Sawan et al. |
| 2006/0111757 A9 | 5/2006 | Greenberg et al. |
| 2006/0184245 A1 | 8/2006 | Graf et al. |
| 2006/0215049 A1 | 9/2006 | Sandini et al. |
| 2006/0256989 A1 | 11/2006 | Olsen et al. |
| 2006/0282128 A1 | 12/2006 | Tai et al. |
| 2006/0287688 A1 | 12/2006 | Yonezawa |
| 2007/0005116 A1 | 1/2007 | Lo |
| 2007/0123766 A1 | 5/2007 | Whalen et al. |
| 2007/0142877 A1 | 6/2007 | McLean |
| 2007/0142878 A1 | 6/2007 | Krulevitch et al. |
| 2007/0191909 A1 | 8/2007 | Ameri et al. |
| 2008/0114230 A1 | 5/2008 | Addis |
| 2008/0234791 A1 | 9/2008 | Arle et al. |
| 2008/0262571 A1 | 10/2008 | Greenberg et al. |
| 2008/0288036 A1 | 11/2008 | Greenberg et al. |
| 2008/0288067 A1* | 11/2008 | Flood .................... 623/6.63 |
| 2008/0294224 A1 | 11/2008 | Greenberg et al. |
| 2009/0002034 A1 | 1/2009 | Westendorp et al. |
| 2009/0005835 A1 | 1/2009 | Greenberg et al. |
| 2009/0024182 A1 | 1/2009 | Zhang et al. |
| 2009/0118805 A1 | 5/2009 | Greenberg et al. |
| 2009/0192571 A1 | 7/2009 | Stett et al. |
| 2009/0204207 A1 | 8/2009 | Blum et al. |
| 2009/0204212 A1 | 8/2009 | Greenberg et al. |
| 2009/0216295 A1 | 8/2009 | Zrenner et al. |
| 2009/0228069 A1 | 9/2009 | Dai et al. |
| 2009/0287275 A1 | 11/2009 | Suaning et al. |
| 2009/0326623 A1 | 12/2009 | Greenberg et al. |
| 2010/0087895 A1 | 4/2010 | Zhou et al. |
| 2010/0174224 A1 | 7/2010 | Sohn |
| 2010/0204754 A1 | 8/2010 | Gross et al. |
| 2010/0249877 A1 | 9/2010 | Naughton |
| 2010/0249878 A1 | 9/2010 | McMahon et al. |
| 2010/0331682 A1 | 12/2010 | Stein et al. |
| 2011/0054583 A1 | 3/2011 | Litt et al. |
| 2011/0106229 A1 | 5/2011 | Ortmann |
| 2011/0172736 A1 | 7/2011 | Gefen et al. |
| 2011/0254661 A1 | 10/2011 | Fawcett et al. |
| 2012/0035725 A1 | 2/2012 | Gefen et al. |
| 2012/0035726 A1 | 2/2012 | Gross et al. |

(56) References Cited

U.S. PATENT DOCUMENTS

| | | |
|---|---|---|
| 2012/0041514 A1 | 2/2012 | Gross et al. |
| 2012/0194781 A1 | 8/2012 | Agurok |
| 2012/0194871 A1 | 8/2012 | Murata |
| 2012/0209350 A1 | 8/2012 | Taylor et al. |
| 2012/0221103 A1 | 8/2012 | Liran et al. |
| 2012/0259410 A1 | 10/2012 | Gefen et al. |
| 2012/0268080 A1 | 10/2012 | Jeon et al. |
| 2012/0269205 A1 | 10/2012 | Haque et al. |
| 2012/0283800 A1 | 11/2012 | Perryman et al. |
| 2013/0126713 A1 | 5/2013 | Haas et al. |
| 2013/0322462 A1 | 12/2013 | Poulsen |
| 2014/0031931 A1 | 1/2014 | Liran et al. |
| 2014/0047713 A1 | 2/2014 | Singh et al. |

FOREIGN PATENT DOCUMENTS

| | | |
|---|---|---|
| CN | 1875895 | 12/2006 |
| DE | 10315397 | 10/2004 |
| JP | 2000-350742 | 12/2000 |
| JP | 2003-528702 | 9/2003 |
| JP | 20077042569 | 2/2007 |
| WO | WO0191854 | 12/2001 |
| WO | WO03032946 | 4/2003 |
| WO | WO2007006376 | 1/2007 |
| WO | WO2007009539 | 1/2007 |
| WO | WO 2007/076347 | 5/2007 |
| WO | WO2007095395 | 8/2007 |
| WO | WO2010035173 | 4/2010 |
| WO | WO2010089739 | 8/2010 |
| WO | WO2011086545 | 7/2011 |
| WO | WO 2011/163262 | 12/2011 |
| WO | 2012/017426 | 2/2012 |
| WO | 2012/114327 | 8/2012 |
| WO | WO 2012/114327 | 8/2012 |
| WO | WO/2012/153325 | 11/2012 |

OTHER PUBLICATIONS

Extended European Search Report dated Nov. 19, 2013 which issued during the prosecution of Applicant's European Patent Application No. 11814197.7.

J.F. Rizzo, "Methods and Perceptual Thresholds for Short-Term Electrical Stimulation of Human Retina with Microelectrode Arrays", Investigative Ophthalmology and Visual Science, vol. 44, No. 12, (Dec. 1, 2003) pp. 5355-5361.

Normann et al., "High-resolution spatio-temporal mapping of visusal pathways using multi-electrode arrays," Vision Research 41 (2001) 1261-1275.

Notice of Allowance issued in U.S. Appl. No. 13/437,310, dated Jan. 28, 2014.

Weber et al., "Implementations and implications of foveated vision", Recent Patents on Computer Science 2009, 2 75-85.

Schmidhuber et al., "Learning to generate artificial fovea trajectories for target detection", International Journal of Neural Systems, [1991] 2(1 & 2): 135-141.

Park et al., "A foveaed-structured CMOS retina chip for edge detection with local light adaptation", Sensors and Actuators A 108 [2003] 75-80.

An Office Action dated Mar. 3, 2015, which issued during the prosecution of U.S. Appl. No. 13/148,461.

An Office Action dated Feb. 5, 2015, which issued during the prosecution of U.S. Appl. No. 14/199,462.

An Office Action dated Apr. 14, 2015, which issued during the prosecution of U.S. Appl. No. 14/018,850.

An Office Action dated Feb. 3, 2014, which issued during the prosecution of U.S. Appl. No. 13/683,158.

Partial International Search Report issued in PCT/IB2014/067417.

Partial International Search Report issued in PCT/IB2015/050224.

An EP Search Report dated Feb. 20, 2015 that issued in EP 12782462.1.

An International Search Report and Written Opinion, dated Feb. 27, 2014, which issued in the Applicant's PCT Application No. PCT/IB2013/060270.

Examination Report, dated Apr. 16, 2014, which issued in the Applicant's EP Application No. 11732733.8.

Official Action, dated Nov. 27, 2013, which issued in the Applicant's JP Application No. 2011-548843.

Examination Report, dated Feb. 26, 2014, which issued in the Applicant's EP Application No. 10738277.2.

Partial International Search Report, dated Jun. 16, 2014, which issued in the Applicant's PCT Application No. PCT/IB2014/059672.

International Search Report and Written Opinion, dated Nov. 11, 2014, which issued in the Applicant's PCT Application No. PCT/IB2014/059672.

Delbruck et al.: "Analog VLSI Adaptive, Logarithmic, Wide-Dynamic-Range Photoreceptor," 1994 International Symposium on Circuits and Systems (London, 1994), p. 339-342.

Grill W., at al., Implanted Neural Interfaces: Biochallenges and Engineered Solutions, Annu. Rev. Biomed. Eng. 2009, 11:1.

Jourdain R P., at al., "Fabrication of piezoelectric thick-film bimorph micro-actuators from bulk ceramics using batch-scale methods" Multi-Material Micro Manufacture, S. Dimov and W. Menz (Eds.) 2008 Cardiff University, Cardiff, UK., Whittles Publishing Ltd.

Kim B., "Through-Silicon-via Copper Deposition for Vertical Chip Integration" Master. Res, Soc. Symp. Proc. vol. 970, 2007 Material Research Society.

Lianga C, at al., "Surface modification of cp-Ti using femtosecond laser micromachining and the deposition of Ca/P layer" Materials Letters vol. 62, Issue 23, Aug. 31, 2008, pp. 3783-3786—an abstract.

David C Ng, et al., "Pulse frequency modulation based CMOS image sensor for subretinal stimulation" IEEE Transactions on Circuits and Systems—II: Express Briefs, vol. 53, No. 6, Jun. 2006.

News Release—Sony develops back-illuminated CMOS image sensor, realizing high picture quality, nearly twofold sensitivity (*1) and low noise, Jun. 2008 http://www.sony.net/SonyInfo/News/Press/200806/08-069E/index.html.

Puech M., et al., "Fabrication of 3D packaging TSV using DRIE" Alcatel Micro Machining Systems, vvww.adixen.com, Mar. 2007.

Seo J M., et al., "Biocompatibility of polyimide microelectrode array for retinal stimulation," Materials Science and Engineering: C, vol. 24, No. 1, Jan. 5, 2004, pp. 185-189(5).

Sorkin R., et al., "Process entanglement as a neuronal anchorage mechanism to rough surfaces," Nanotechnology 20 (2009) 015101 (8pp).

Starzyk JA, et al., "A DC-DC charge pump design based on voltage doublers" IEEE Transaction on Circuits and Systems—I: Fundamental theory and applications, vol. 48, No. 3 Mar. 2001.

Stein DJ, et al., "High voltage with Si series photovoltaics" Proceedings of SPE, the International Society for Optical Engineering 2006, vol. 6287, pp. 62870D.1-62870D, (an abstract).

Swain P K., et al., "Back-Illuminated Image Sensors Come to the Forefront. Novel materials and fabrication methods increase quality and lower cost of sensors for machine vision and industrial imaging." Photonics Spectra Aug. 2008.

Vorobyeva A Y. at al., "Metallic light absorbers produced by femtosecond laser pulses," Advances in Mechanical Engineering vol. 2010, Article ID 452749, 4 pages doi:10.1155/2010/452749, Hindawi Publishing Corporation.

Vorobyeva A Y. et al., "Femtosecond laser structuring of titanium implants," Applied Surface Science vol. 253, Issue 17, Jun. 30, 2007, pp. 7272-7280—an abstract.

Wallman L., et al., "The geometric design of micromachined silicon sieve electrodes influences functional nerve regeneration," Biomaterials May 2001:22(10):1 187-93, (an abstract).

Walter P., et al., "Cortical Activation via an implanted wireless retinal prosthesis," Investigative Ophthalmology and Visual Science. 2005;46:1780-1785.

Wu J T. and Chang K L., "MOS charge pumps for low-voltage operation" IEEE Journal of Solid-State Circuits, vol. 33 No. 4 Apr. 1998.

Zrenner E., 2002. "Will retinal implants restore vision?" Science 295(5557), pp. 1022-1025.

(56) References Cited

OTHER PUBLICATIONS

Office Action dated Aug. 24, 2011 issued during the prosecution of related U.S. Appl. No. 12/368,150.
International Preliminary Report on Patentability and Written Opinion dated Aug. 9, 2011, issued in related International Application No. PCT/IL2010/000097.
International Search Report dated Aug. 17, 2010, issued in related International Application No. PCT/IL2010/000097.
International Search Report and Written Opinion dated Aug. 12, 2011, issued in related International Application No. PCT/IL2011/000022.
International Search Report and Written Opinion dated Dec. 12, 2011 issued in related International Application No. PCT/IL2011/00609.
An Office Action dated Aug. 28, 2012, which issued during the prosecution of U.S. Appl. No. 12/852,218.
An Office Action dated Sep. 28, 2012, which issued during the prosecution of U.S. Appl. No. 13/103,264.
An International Preliminary Report on Patentability dated Jul. 17, 2012, which issued during the prosecution of Applicant's PCT/IL2011/000022.
A Supplementary European Search Report dated Aug. 10, 2012, which issued during the prosecution of Applicant's European Application No. 10 73 8277.
Palanker D. et al., "Design of a high-resolution optoelectric retinal prosthesis". Journal of Neural Engineering, Institute of physics publishing, Bristol, GB. vol. 2, No. 1, Mar. 1, 2005, pp. S105-S120, XP002427333, ISSN: 17412552, DOI: 10.1088/1741-2560/2/11012.
Cortical Visual Neuro-Prosthesis for the Blind: Retina-Like Software/Hardware Preprocessor, F.J. Pelayol, A. Martinezl, S. Romerol, Ch.A. Morillasl, E. Rosl , E. Fernandez2 1Dept. of Computer Architecture and Technology, University of Granada, Spain 2Dept. of Histology and Institute of Bioengineering, University Miguel Hernandez, Alicante, Spain Neural Engineering, 2003. Conference Proceedings. First International IEEE EMBS Conference.
"Single-Chip CMOS Image Sensors for a Retina Implant System", Markus Schwarz, Ralf Hauschild, Bedrich J. Hosticka, Senior Member, IEEE, Jurgen Huppertz, Student Member, IEEE, Thorsten Kneip, Member, IEEE, Stephan Kolnsberg, Lutz Ewe, and Hoc Khiem Trieu, 2000.
An International Search Report dated Aug. 12, 2011, which issued during the prosecution of Applicant s PCT/IL2011/000022.
An International Search Report and a Written Opinion both dated Sep. 17, 2012, which issued during the prosecution of Applicant's PCT/IL12/00057.
Schwarz et al. "Hardware Architecture of a Neural Net Based Retina Implant for Patients Suffering from Retinitis Pigmentosa," Fraunhofer Institute of Microelectronic Circuits and Systems, pp. 653-658 (1996).
Ganesan et al. "Diamond Penetrating Electrode Array for Epi-Retinal Prosthesis," 32nd Annual International Conference of the IEEE EMBS, pp. 6757-6760 (2010).
Finn, et al. "An Amphibian Model for Developing and Evaluating Retinal Prostheses," 18th Annual International Conference of the IEEE Engineering in Medicine and Biology Society, pp. 1540-1541 (1996).
Shawn Kelly, "A System for Electrical Retinal Stimulation for Human Trials," Massachusetts Institute of Technology, pp. 1-45 (1998).
Andreou et al. "Analog Integrated Circuits and Signal Processing," An International Journal, vol. 9, No. 2, pp. 141-166 (1996).
Office Action for U.S. Appl. No. 13/034,516 dated Dec. 14, 2012.
Office Action for U.S. Appl. No. 12/687,509 dated Dec. 7, 2012.
Office Action for U.S. Appl. No. 13/148,461 dated Mar. 13, 2013.
Office Action for U.S. Appl. No. 12/687,509 dated Jun. 6, 2013.
International Search Report and Written Opinion for International Application No. PCT/IL2012/000186 dated Sep. 4, 2012.
Humayun et al. Visual perception in a blind subject with a chronic microelectronic retinal prosthesis, Vision Research, vol. 43, pp. 2573-2581 (2003).
Tran et al. "A Fully Flexible Stimulator using 65 nm CMOS Process for 1024-electrode Epi-retinal Prosthesis," 31st Annual International Conference of the IEEE EMBS, pp. 1643-1646 (2009).
Office Action issued in U.S. Appl. No. 13/437,310, dated Aug. 12, 2013.
An interview summary in U.S. Appl. No. 13/437,310 dated Nov. 14, 2013 in connection with the Office Action issued on Aug. 12, 2013.
European Search Report for European Application No. EP11732733 dated Jul. 16, 2013.
Yoo et al. "Excimer laser deinsulation of Parylene-C on iridium for use in an activated iridium oxide film-coated Utah electrode array," Journal of Neuroscience Methods, 215 (2013) 78-87.
Schmidhuber, J., "Learning to generate artificial fovia trajectories for target detection," International Journal of Neurosystems; 2(1 & 2):135-141, (1991).
ISR and the Written Opinion issued on Jun. 30, 2015 in PCT/IB2014/067417.
The ISR and the Written Opinion issued on Jun. 30, 2015 in PCT/IB2015/050224.
The Office Action as issued in U.S. Appl. No. 14/160,314 on Aug. 20, 2015.

* cited by examiner

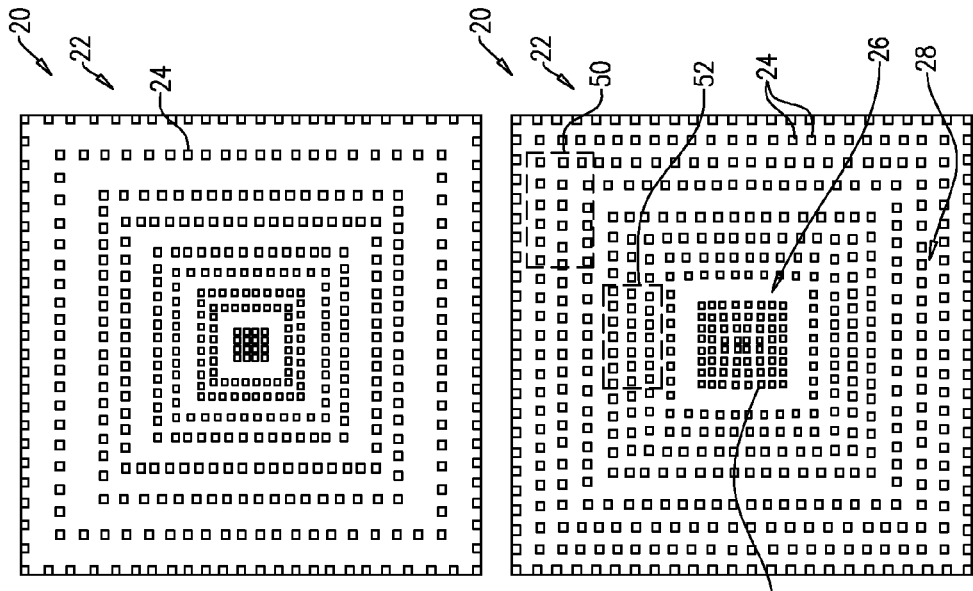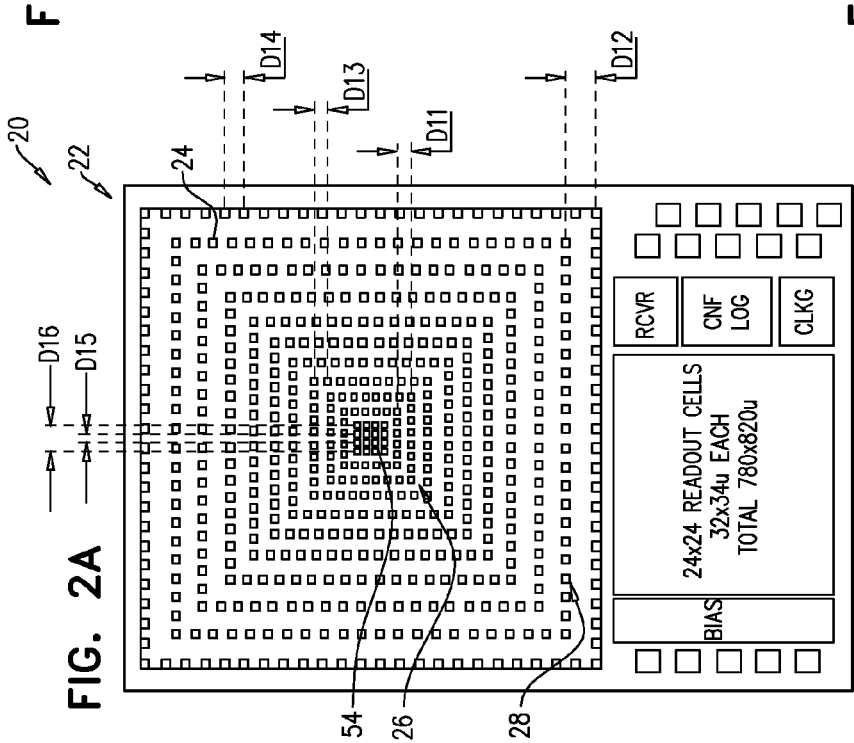

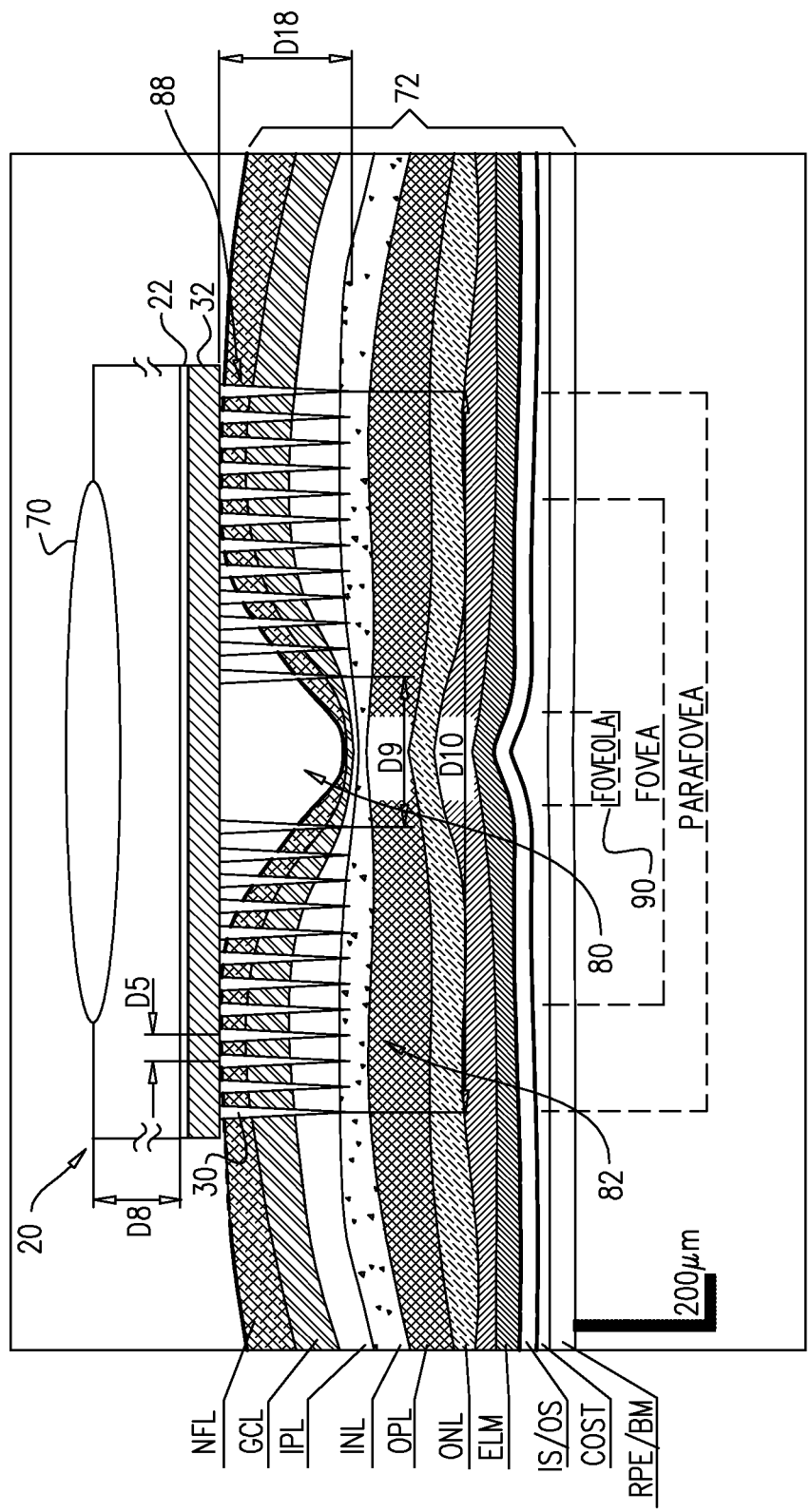

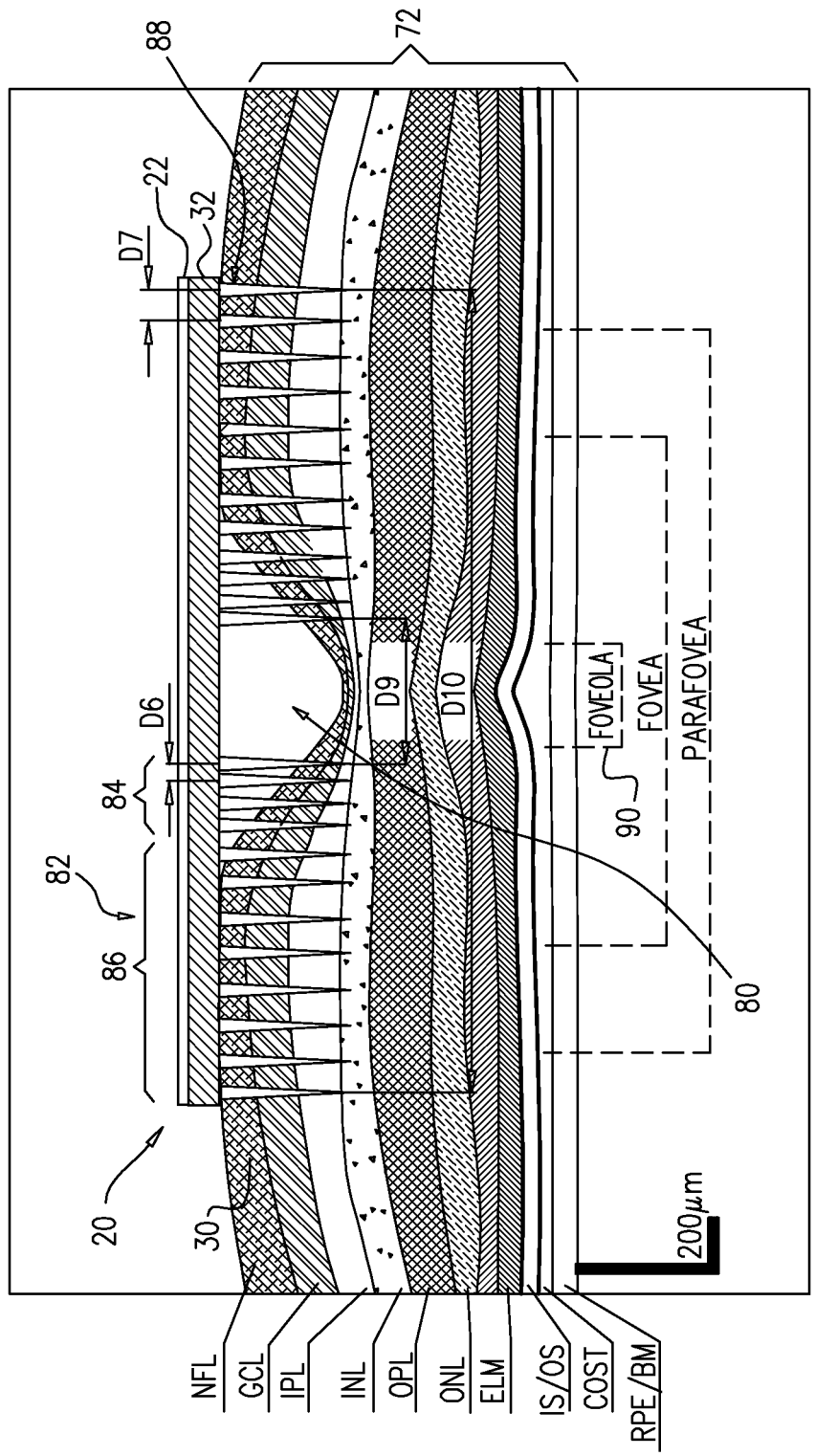

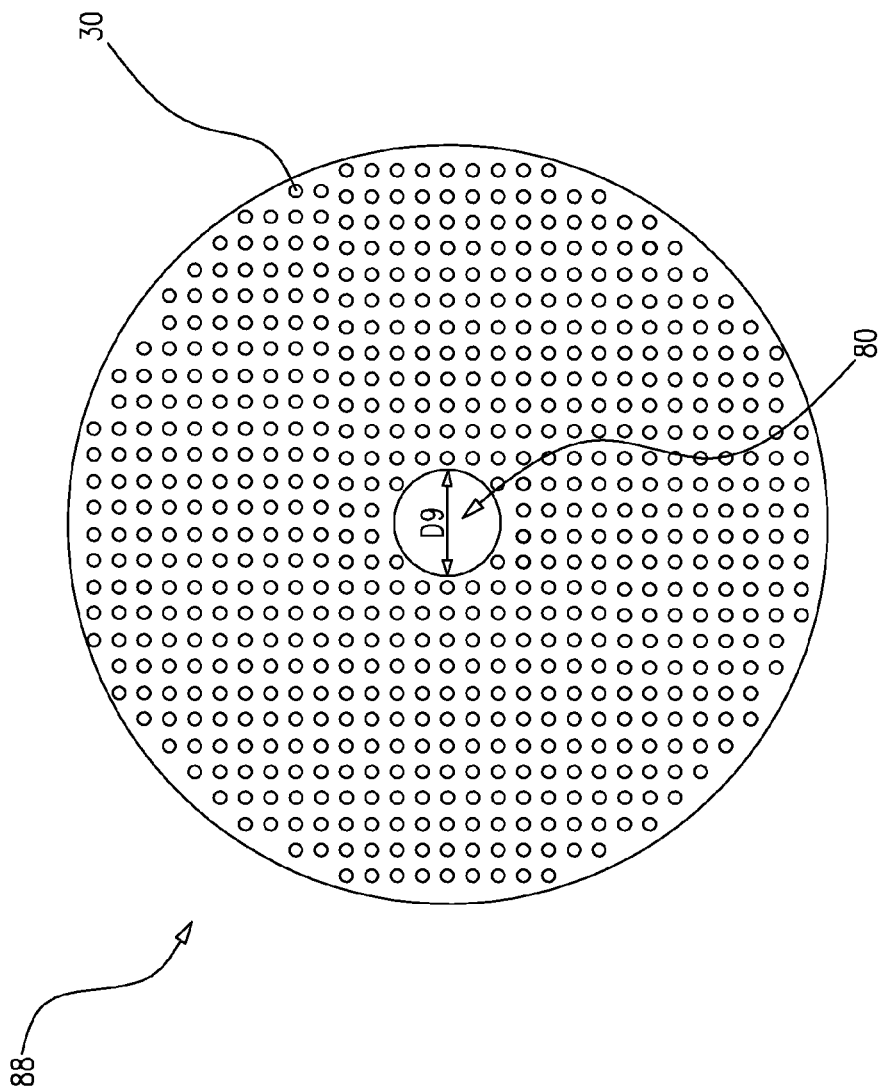

FOVEATED RETINAL PROSTHESIS

FIELD OF THE APPLICATION

Applications of the present invention relate generally to implantable medical devices, and specifically to a retinal prosthesis.

BACKGROUND OF THE APPLICATION

Retinal malfunction, due to degenerative retinal diseases, is a leading cause of blindness and visual impairment. Implantation of a retinal prosthesis is a technology for restoring some useful vision in individuals suffering from retinal-related blindness.

The retina is a multi-layered light-sensitive structure that lines the posterior, inner part of the eye. The retina contains photoreceptor cells, for example rods and cones, which capture light and convert light signals into neural signals transmitted through the optic nerve to the brain. Rods are responsible for light sensitive, low resolution black and white vision, whereas cones are responsible for sharp, high resolution color vision. Most cones lie in the fovea, which defines the center of the retina, and which allows for maximum acuity of vision. The central portion of the fovea consists of a high concentration of cones that gradually decreases at the peripheral portions of the fovea.

SUMMARY OF APPLICATIONS

For some applications, a foveated retinal prosthesis is provided comprising a space-variant photosensor imager. The retinal prosthesis is typically configured to provide at least some sharp, central, foveal vision to a visually-impaired subject. In accordance with some applications of the present invention, an intraocular device is provided which is configured to be implanted entirely in the subject's eye. The intraocular device typically comprises a space-variant photosensor array which comprises a plurality of photosensors, each photosensor configured to detect ambient photons and generate a signal in response thereto. The intraocular device additionally comprises a plurality of stimulating electrodes. Driving circuitry is coupled to the photosensors and is configured to drive the electrodes to apply electrical pulses to a retina of the eye in response to the signal from the photosensors.

Typically, the photosensor array is arranged such that a spatial density of the photosensors in a central portion of the array is greater than a spatial density of the photosensors in an outer portion of the array, resembling the structure of a native fovea of a retina. Additionally, for some applications, an intermediate portion of the photosensor array is disposed between the central portion and the outer portion of the array. Typically, a spatial density of the photosensors in the intermediate portion is between (a) the spatial density of the photosensors in the central portion and (b) the spatial density of the photosensors in the outer portion.

For some applications, the intermediate portion of the photosensor array comprises a plurality of intermediate portions, each having a different, respective spatial density of the photosensors. Thus, a stepped decrease or a smooth decrease in photosensor spatial density may be provided in alternative configurations.

For some applications the photosensor array comprises an array of at least 10 clusters of two or more photosensors. The clusters typically comprise 4-64 photosensors. For such applications, the spatial density of the photosensors in a cluster disposed in the central portion of the array is greater than the spatial density of the photosensors in a cluster disposed in the outer portion of the array.

For some applications, the plurality of stimulating electrodes are arranged in an array in a manner in which a spatial density of the electrodes in the array is constant (optionally, excluding that portion of the array which is over the foveola). For other applications, the spatial density of the electrodes in the central portion of the electrode array (optionally, excluding a portion that is over the foveola) is greater than the spatial density of the electrodes in the outer portion of the electrode array, e.g., to reduce any perceived spatial distortion of the image, whereby the inner portion of the image would appear magnified due to the foveation of the photosensor array.

There is therefore provided, in accordance with some applications of the present invention, apparatus, including an intraocular device configured to be implanted entirely in a subject's eye, the intraocular device including:

a photosensor array including a plurality of photosensors, each photosensor configured to detect ambient photons and to generate a signal in response thereto, a spatial density of the photosensors in a central portion of the array being greater than a spatial density of the photosensors in an outer portion of the array;

a plurality of stimulating electrodes; and driving circuitry, coupled to the photosensors, and configured to drive the electrodes to apply electrical pulses to a retina of the eye in response to the signals from the photosensors.

For some applications, a spatial density of the photosensors in an intermediate portion of the array disposed between the central portion and the outer portion is between (a) the spatial density of the photosensors in the central portion and (b) the spatial density of the photosensors in the outer portion.

For some applications, the intermediate portion of the array includes a plurality of intermediate portions, each having a different, respective spatial density of the photosensors, any given intermediate portion that is closer to the central portion having a spatial density higher than that of any intermediate portion that is farther than the given intermediate portion from the central portion.

For some applications, the photosensor array includes at least two clusters of four or more photosensors, the photosensors in each cluster having a respective generally-uniform spatial density, the spatial density of the photosensors in one of the clusters that is disposed nearer the central portion of the array is greater than the spatial density of the photosensors in one of the clusters that is disposed nearer the outer portion of the array.

For some applications, the at least two clusters of four or more photosensors include at least ten clusters of four or more photosensors.

For some applications, the plurality of stimulating electrodes are arranged in an array, a spatial density of the electrodes being constant.

For some applications, the plurality of stimulating electrodes are arranged in an electrode array, a spatial density of the electrodes in a central portion of the electrode array being greater than a spatial density of the electrodes in an outer portion of the electrode array.

There is additionally provided, in accordance with some applications of the present invention, apparatus including an intraocular device configured to be implanted entirely in a subject's eye, the intraocular device including:

a photosensor array including a plurality of photosensors, each photosensor configured to detect ambient photons and to generate a signal in response thereto, an optical magnifying element coupled to the photosensor array and configured to provide a magnified image on some but less than all of the photosensors of the photosensor array;

a plurality of stimulating electrodes; and driving circuitry, coupled to the photosensors, and configured to drive the electrodes to apply electrical pulses to a retina of the eye in response to the signals from the photosensors.

There is further provided, in accordance with some applications of the present invention, apparatus including an intraocular device configured to be implanted entirely in a subject's eye, the intraocular device including:

a photosensor array including a plurality of photosensors, each photosensor configured to detect ambient photons and to generate a signal in response thereto;

an arrangement of stimulating electrodes, a spatial density of the electrodes in a central portion of the arrangement being lower than a spatial density of the electrodes in an outer portion of the arrangement, the arrangement being such that: (a) the outer portion surrounds the central portion, and (b) the central portion is large enough to contain therewithin a circle of diameter at least 100 um; and driving circuitry, coupled to the photosensors, and configured to drive the electrodes to apply electrical pulses to a retina of the eye in response to the signals from the photosensors.

For some applications, the spatial density of the electrodes in the central portion is zero, and the spatial density of the electrodes in the outer portion is at least 4 electrodes per mm^2.

For some applications, the outer portion of the arrangement includes at least first and second sub-portions, the second sub-portion surrounding the first sub-portion, a spatial density of the electrodes in the second sub-portion of the arrangement being lower than a spatial density of the electrodes in the first sub-portion.

For some applications, the central portion is large enough to contain therewithin a circle of diameter of 100 um.

There is also provided, in accordance with some applications of the present invention, apparatus, including:

an intraocular device configured to be implanted entirely in a subject's eye, the intraocular device including:

a photosensor array, having a center thereof, and including a plurality of photosensors, each photosensor configured to detect ambient photons and to generate a signal in response thereto;

an array of stimulating electrodes, having a center thereof, and coupled to the photosensor array; and driving circuitry, coupled to the photosensors, and configured to drive an electrode located at a first distance from the center of the electrode array to apply electrical pulses to a retina of the eye in response to a signal from a photosensor located at a second distance from the center of the photosensor array, the first distance being greater than the second distance.

The present invention will be more fully understood from the following detailed description of embodiments thereof, taken together with the drawings, in which:

BRIEF DESCRIPTION OF THE DRAWINGS

FIGS. 2A-E are schematic illustration of alternative configurations of a photosensor array for use in the implantable intraocular device of FIG. 1, in accordance with respective applications of the present invention;

FIGS. 3A-B are schematic illustration of an array of stimulating electrodes implanted in an eye of the subject, for use with any of the photosensor arrays shown in FIGS. 1-2, in accordance with respective applications of the present invention;

FIGS. 5A-B are schematic illustrations of a bottom view of an array of stimulating electrodes implantable in an eye of the subject, for use with any of the photosensor arrays shown in FIGS. 1-2, in accordance with respective applications of the present invention.

DETAILED DESCRIPTION OF APPLICATIONS

Figure 1:
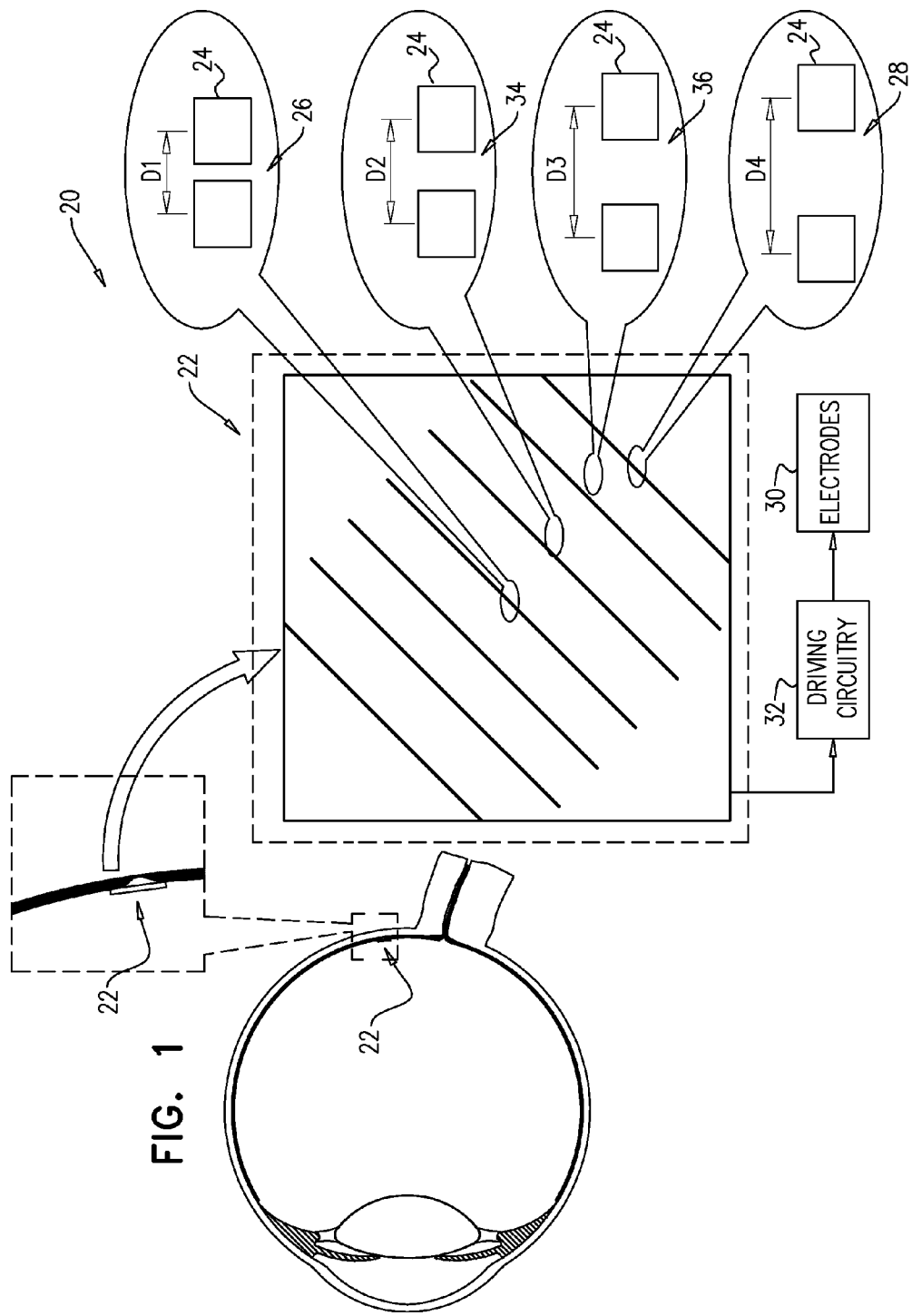
FIG. 1 is a schematic illustration of a photosensor array for use in an implantable intraocular device, in accordance with some applications of the present invention.

Reference is made to FIG. 1, which is a schematic illustration of a photosensor array 22 configured for use as part of an implantable intraocular device 20, in accordance with some applications of the present invention. Photosensor array 22 comprises a plurality of photosensors 24, each photosensor 24 configured to detect ambient photons and to generate a signal in response thereto. Driving circuitry 32, coupled to photosensors 24, drives a plurality of stimulating electrodes 30 to apply electrical pulses to a retina of the eye in response to the signal from the photosensors.

As shown schematically in FIG. 1, photosensor array 22 is arranged such that a spatial density of photosensors 24 in a central portion 26 of array 22 is greater than a spatial density of photosensors 24 in an outer portion 28 of array 22. As shown, a distance D1 between two photosensors 24 disposed in central portion 26 is smaller than a distance D4 between two photosensors 24 disposed in outer portion 28. For example, D1 is typically greater than 2 um and/or less than 100 um, e.g., greater than 4 um and/or less than 50 um. D4 is typically greater than 40 um and/or less than 1000 um, e.g., greater than 100 um and/or less than 500 um (e.g., 300 um). D4 divided by D1 is typically at least 2 (e.g., at least 4) and/or less than 200.

For some applications, the spatial density of the photosensors in an intermediate portion 34 of the array disposed between central portion 26 and outer portion 28 is between (a) the spatial density of the photosensors in central portion 26 and (b) the spatial density of the photosensors in outer portion 28. For example, a distance D2 between photosensors in intermediate portion 34 is between D1 and D4.

Photosensor array 22 may similarly be arranged to have a plurality of intermediate portions 34 and 36, each having a different, respective spatial density of photosensors 24. In such an arrangement, any given intermediate portion 34 that is closer to central portion 26 has a spatial density higher than that of any intermediate portion 36 that is farther than given intermediate portion 34 from central portion 26. Photosensor array 22 may be arranged to have 2, 3, 4-6, 7-10, or more intermediate portions. (Two intermediate portions 34 and 36 are shown in FIG. 1.)

Figure 2E:
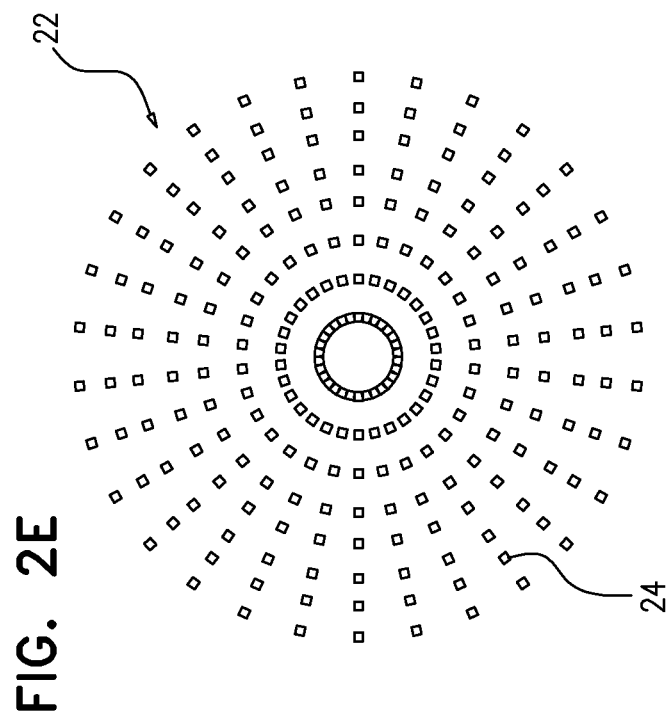
Figure 2D:
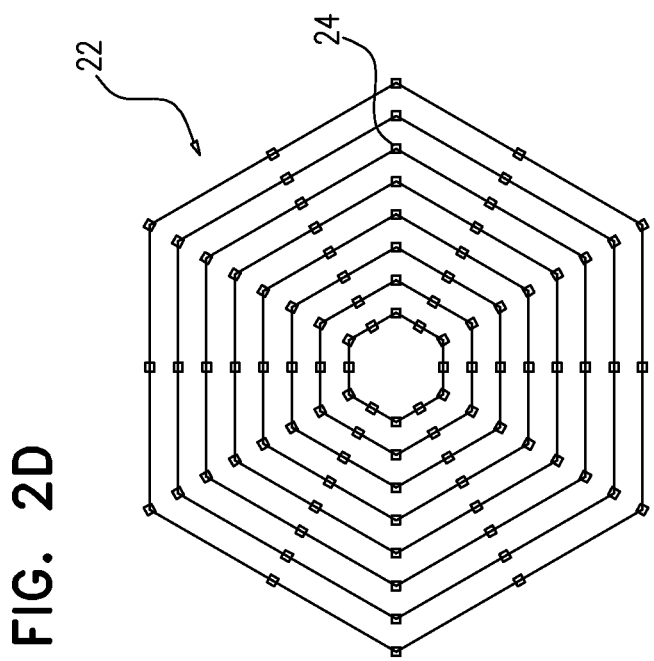

FIG. 2A is a schematic illustration of photosensor array 22, in which photosensors 24 are arranged in concentric rings, in accordance with some applications of the present invention. As shown in the figures of the present patent application, the rings of photosensors are square rings, although the scope of the present invention includes the use of concentric rectangular, circular, hexagonal, and elliptical rings, as well as concentric rings of other shapes. Examples of hexagonal and circular photosensor arrays are shown in FIGS. 2D-E (respectively).

Each ring of photosensors 24 shown in FIG. 2A has the photosensors thereof disposed with a given distance D13 separating adjacent photosensors in the same ring. Photosensor array 22 as shown in FIG. 2A is characterized in that the distance D13 between photosensors in a ring closer to central portion 26 is smaller than the distance D14 between photosensors in a ring farther from central portion 26. In the application shown in FIG. 2A, successive rings going from central portion 26 toward outer portion 28 have gradually increasing, and typically monotonically increasing, distances between photosensors in each successive ring.

Alternatively or additionally, the distance between successive rings increases (typically monotonically) from a smaller distance D11, nearer central portion 26, to a larger distance D12, farther from central portion 26.

As shown in FIG. 2A and other figures, for some applications the rings of photosensors 24 may surround a central core 54 of photosensors, which are not arranged as a ring. Central core 54 typically comprises 4-100 photosensors 24. For some applications, the photosensors in central core 54 are spaced from each other by a distance D15 of 4-30 um, and/or central core 54 itself has a length D16 of 16-300 um as its longest dimension. For some applications, D16 is greater than 300 um (e.g., as shown in FIG. 2C).

For some applications, the number of photosensors 24 in each successive ring is constant, even though the perimeter of the ring increases. Alternatively, the number of photosensors increases, but not as fast as the perimeter of the ring. Still further alternatively, the number of photosensors in each increases as fast as the perimeter of the ring (i.e., a ring having twice as many photosensors as a more central ring also has twice the perimeter of the more central ring), however the space between successive rings increases (e.g., from D11 to D12 as shown).

As appropriate based on the amount of photosensor foveation desired in a given design, the increase in ring spacing (e.g., D11 to D12) and/or the increase in intra-sensor spacing (e.g., D13 to D14) may follow, for example, an arithmetic progression (k, 2k, 3k . . . ) or a geometric progression (1, k, k^2, k^3 . . . ). Typically, arithmetic progression spacing produces gradual spatial distortion of the image, which generally allows for rapid cognitive adjustment of the subject to a new implant.

FIG. 2B is a schematic illustration of photosensor array 22, in which photosensors 24 are arranged in concentric rings, having geometric or another progression spacing, in accordance with another application of the present invention. Typically, in applications in which photosensors 24 are arranged in concentric rings having geometric progression spacing, array 22 is particularly space efficient. This is generally due to the high spatial density of photosensors 24 in the central portion of the array and a rapid decrease in spatial density of photosensors 24 in the outer portion of the array. The apparatus of FIG. 2B is generally similar to that of FIG. 2A, except for differences as noted herein.

FIG. 2C is a schematic illustration of photosensor array 22, in which photosensors 24 are arranged in clusters (e.g., 1, 1, 2, 2 . . . ), in accordance with another application of the present invention. Typically, photosensor array 22 comprises at least two clusters of four or more photosensors 24. The photosensors in each cluster typically have a respective generally-uniform spatial density, and the spatial density of the photosensors in a cluster 52 that is disposed nearer central portion 26 of the array is greater than the spatial density of the photosensors 24 in a cluster 50 that is disposed nearer outer portion 28 of array 22.

The clusters of photosensors 24 as shown in FIG. 2C are two-dimensional, thus creating array 22 not just with concentric rings of photosensors that have respective densities, but with two-dimensional regions of the array that have particular spatial densities.

Typically, arrangement of photosensors 24 in clusters creates an increased area with constant pixel spacing in central portion 26 of the array, resulting in reduced spatial distortion of the image.

Reference is made to FIGS. 1-2E. For some applications, a size of photosensors 24 is varied across array 22. For example, the size of photosensors 24 in central portion 26 of array 22 may be smaller than the size of photosensors 24 in outer portion of array 22. Variable-sized photosensors may be used in combination with a space-variant array or, alternatively, with an array having constant spacing of photosensors. Alternatively or additionally, the signals generated by multiple photosensors 24 in outer portion 28 of array 22 are used to regulate current delivered from a smaller number of electrodes, e.g., a single electrode (which may be useful in low-light conditions, for example).

Alternatively, for some applications, the array of photosensors is arranged to provide first and second portions, e.g., left and right portions, rather than central and outer portions. For such applications, the photosensor array is arranged such that a spatial density of the photosensors in the first portion of the array is greater than a spatial density of the photosensors in the second portion of the array (application not shown).

Reference is made to FIGS. 3A and 3B, which are schematic cross-sectional illustrations of intraocular device 20, comprising photosensor array 22 (e.g., as described hereinabove with reference to any of the figures) and an array 88 of stimulating electrodes 30 that are epiretinally implanted in the retina 72 of the subject, in accordance with some applications of the present invention.

Intraocular device 20 as shown in FIGS. 3A and 3B comprises an arrangement of stimulating electrodes 30, in which a spatial density of the electrodes in a central portion 80 of the arrangement is lower than a spatial density of the electrodes in an outer portion 82 of the arrangement. In this arrangement, outer portion 82 surrounds central portion 80.

Central portion 80 typically has a length (e.g., a diameter) D9 of 50-1000 um, e.g., 100-500 um, so as to generally cover foveola 90. In any case, central portion 80 is at least large enough to contain therewithin a circle of diameter D9 of 50-1000 um, e.g., a circle of diameter 100-500 um, e.g., a circle of diameter 100-300 um.

Central portion 80 is typically placed over the foveola 90 of the patient's retina, such that typically no electrodes, or only a small number of electrodes are placed in the foveola (e.g., within but near the edge of the circle having diameter D9). In any case, the spatial density of electrodes in central portion 80 that are placed in the foveola is lower than the spatial density of electrodes in outer portion 82 that are placed in retinal tissue outside of the fovea or parafovea outside of the foveola. For example, the spatial density of electrodes in central portion 80 that are placed in the foveola may be zero if, as shown in FIGS. 3A and 3B, central portion 80 has no electrodes. For some applications, the spatial density of the electrodes in the central portion is zero, and the spatial density of the electrodes in the outer portion is at least 4 electrodes per mm^2 (for example, at least 10 electrodes per mm^2, and/or less than 400 or less than 100 electrodes per mm^2).

Figure 4A:
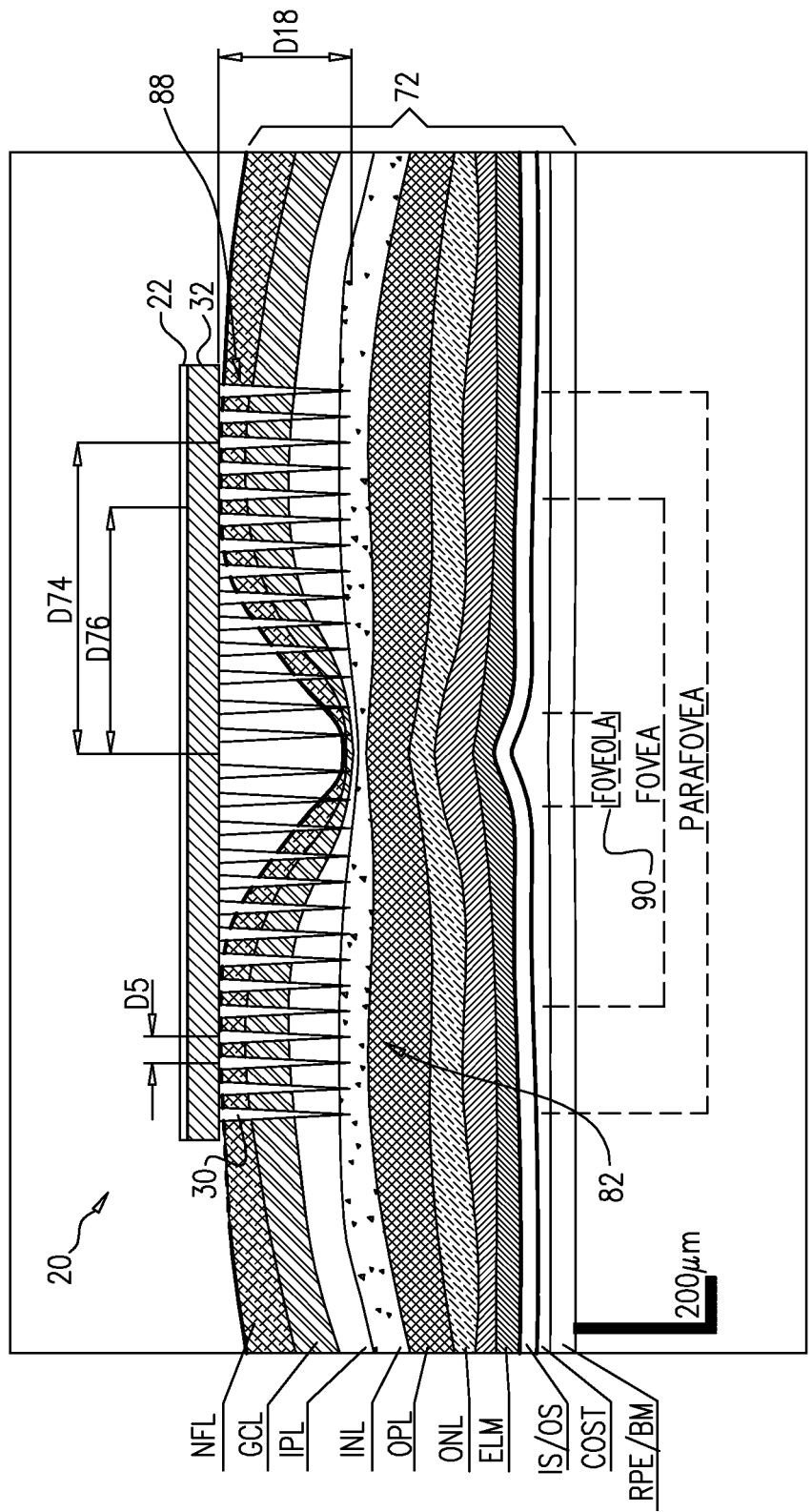
FIGS. 4A-B are schematic illustration of an array of stimulating electrodes implantable in an eye of the subject, for use with any of the photosensor arrays shown in FIGS. 1-2, in accordance with respective applications of the present invention.
Figure 4B:
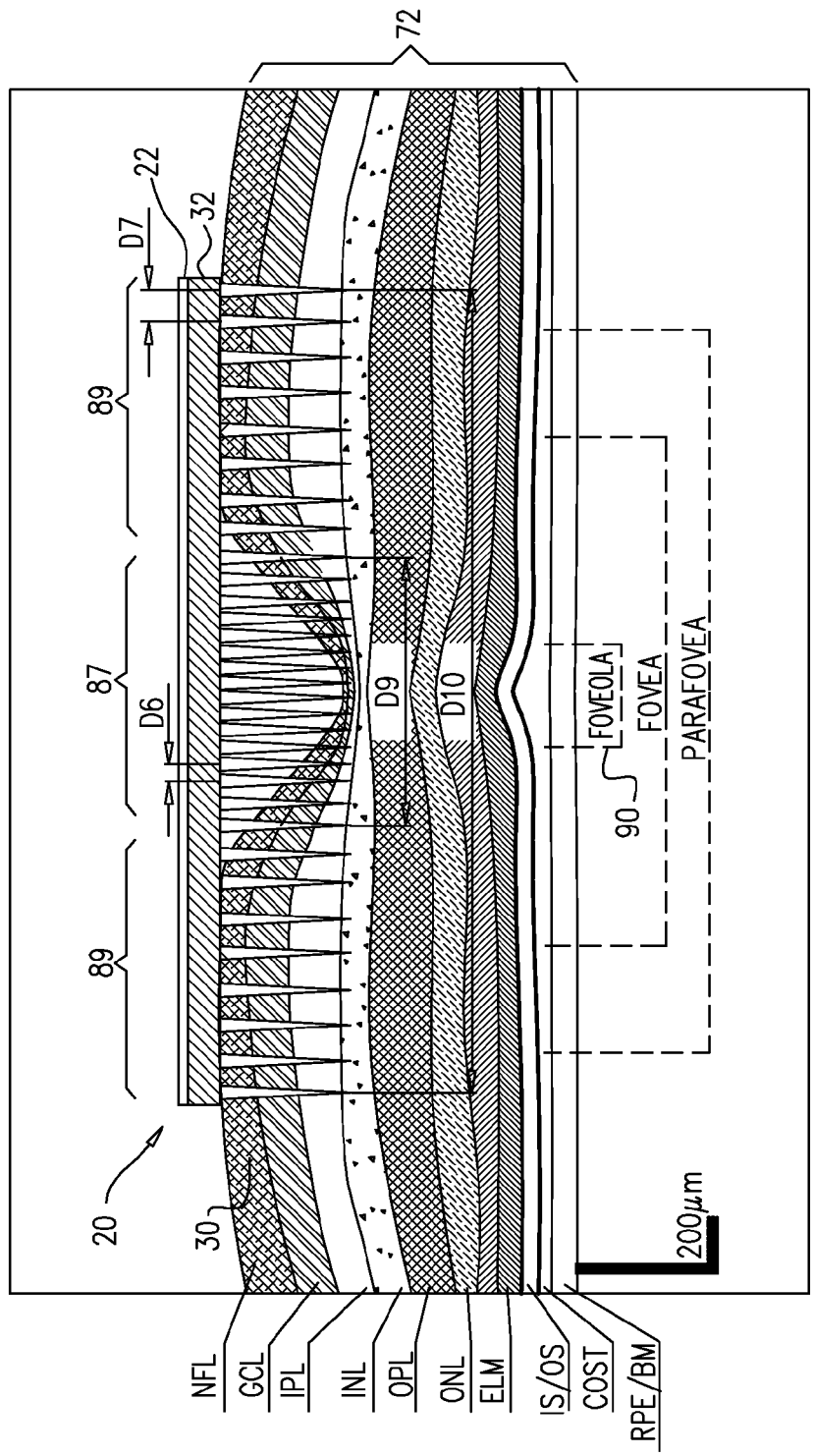

Alternatively, central portion 80 comprises any number of electrodes (e.g., as shown in FIGS. 4A-B) and implantable intraocular device 20 is configured such that driving circuitry 32 does not drive stimulating currents into the electrodes that are located in central portion 80. For such applications, electrodes 30 in central portion 80 may function to anchor device 20 to the retina and not to drive stimulating currents into the retina.

Further alternatively, central portion 80 that is placed over foveola 90 does not comprise electrodes, but rather comprises an anchoring element, e.g., a metallic tack, configured to facilitate anchoring of device 20 to the retina of the subject.

The retina includes a number of identified layers, each having its own properties. These layers include the nerve fiber layer (NFL), ganglion cell layer (GCL), inner plexiform layer (IPL), inner nuclear layer (INL), outer plexiform layer (OPL), outer nuclear layer (ONL), external limiting membrane (ELM), photoreceptor inner segments (IS) and outer segments (OS), cone photoreceptor outer segment tips (COST), and retinal pigment epithelium/Bruch's membrane (RPE/BM). Electrodes 30 typically have a length D18 of at least 50 um and/or less than 500 um, in order to facilitation penetration of the retina. For some applications of the present invention it is intended for electrodes 30 to penetrate the retina and stimulate a layer that is largely not present in the foveola but which is relatively thick in the surrounding fovea and parafovea (e.g., the inner nuclear layer and/or the ganglion cell layer). For these applications, electrodes 30 are typically arranged to provide central portion 80 as described, so as not to provide stimulation intended to generate perception of an image on a part of the retina (the foveola) that does not have significant ganglionic processing.

Typically, as shown in FIG. 3A, stimulating electrodes 30 are arranged in an array, a spatial density of electrodes in outer portion 82 being constant (e.g., 100 um). For example, a distance D5 between adjacent electrodes is typically greater than 10 um and/or less than 500 um. For applications in which the array of electrodes 30 is arranged as a square or a rectangular array, a longest row or column of the array typically has a length D10 greater than 1 mm and/or less than 6.0 mm, e.g., 2-4 mm, so as to generally cover the parafovea. For other arrangements of the electrodes (e.g., concentric circles of electrodes as shown in the bottom view of electrode arrays in FIGS. 5A-B), such values for D10 represent a furthest distance between two electrodes in the array (e.g., a diameter of the circle).

For some applications, an optical magnifying element 70 comprising a single lens (as shown) or a plurality of lenses (e.g., as a telescope, configuration not shown) is coupled to photosensor array 22 and provides a magnified image on some but less than all of photosensors 24 of photosensor array 22. Typically, element 70 is disposed a distance D8 of at least 1 mm and/or less than 30 mm (e.g., less than 15 mm) from photosensor array 22. This arrangement provides magnification of the image being viewed, may be used in combination with, or in the absence of, a variation in spatial density of the photosensors as described hereinabove.

Reference is made to FIG. 3B. For some applications, outer portion 82 of the arrangement comprises at least first and second sub-portions 84 and 86, the second sub-portion surrounding the first sub-portion. The spatial density of the electrodes in second sub-portion 86 of the arrangement is lower than the spatial density of the electrodes in first sub-portion 84, e.g., in order to provide higher spatial stimulation resolution in portions of the retina having the ability to perform more ganglionic processing of incoming visual information. For example, electrodes 30 in sub-portion 84 may be separated by a distance D6 that is at least 10 um and/or less than 100 um, while electrodes 30 in sub-portion 86 may be separated by a distance D7 that is at least 300 um and/or less than 500 um.

Reference is made to FIGS. 4A-B, which are schematic illustrations of array 88, in accordance with respective applications of the present invention. For some applications, array 88 does not comprise a portion 80 that does not have electrodes as described hereinabove with reference to FIGS. 3A-B. As shown in FIG. 4A, stimulating electrodes 30 are arranged in array 88 such that a spatial density of electrodes across the array is constant (e.g., with an interelectrode spacing of 100 um). Alternatively, as shown in FIG. 4B, array 88 comprises a central portion 87 and an outer portion 89, and a spatial density of the electrodes in central portion 87 is greater than the spatial density of the electrodes in outer portion 89 of array 88.

Figure 5A:
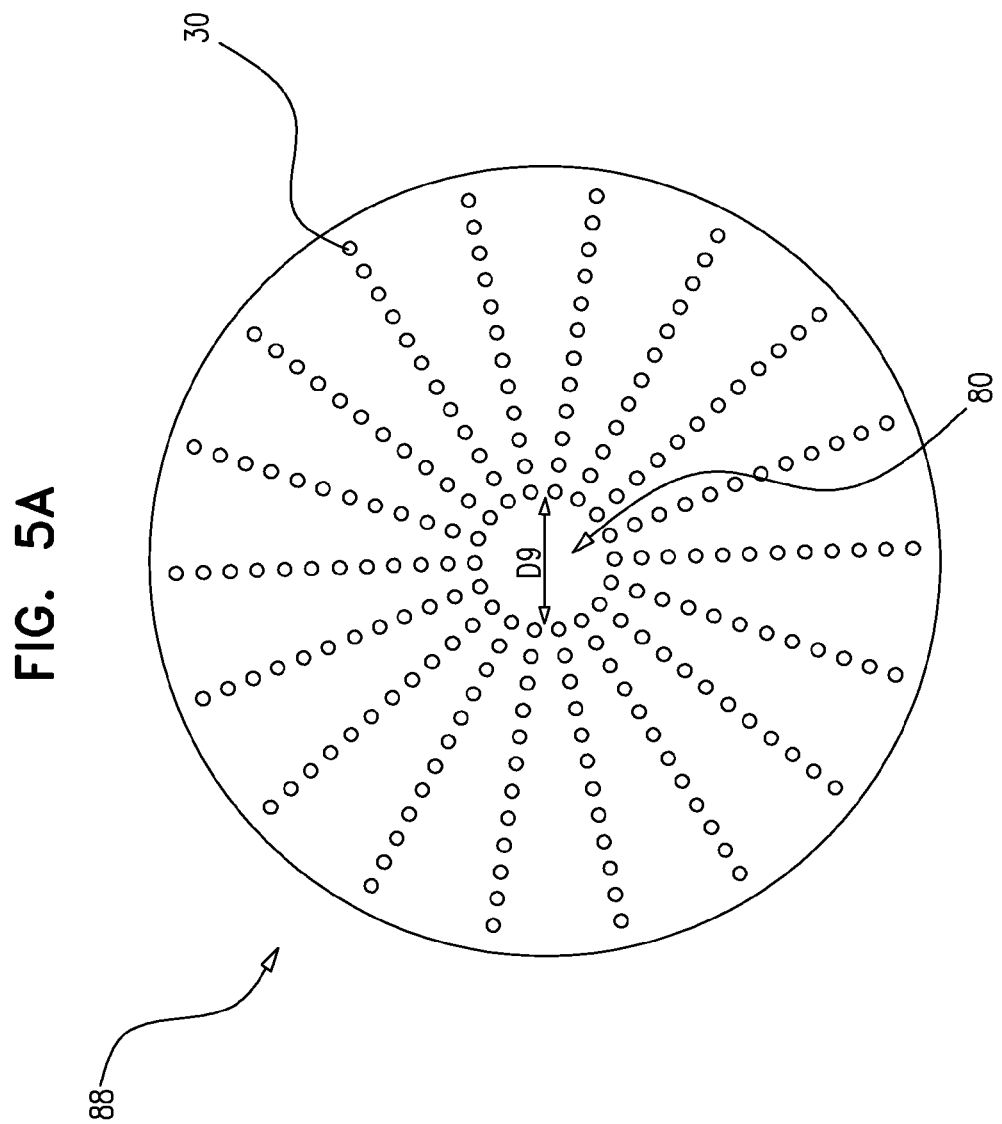

Reference is made to FIGS. 5A-B, which are schematic illustration of bottom views of array 88 of stimulating electrodes 30 implantable in an eye of the subject, for use with any of the photosensor arrays shown in FIGS. 1-2, in accordance with respective applications of the present invention. As shown in FIGS. 5A-B, for some applications, arrays 88 comprises a central portion 80 which is typically at least large enough to contain therewithin a circle of diameter D9 of 50-1000 um, e.g., a circle of diameter 100-500 um, e.g., a circle of diameter 100-300 um.

Reference is made to FIGS. 1-5B. For some applications, photosensor array 22 and array 88 of electrodes 30 have a similar spatial distribution such that the location of each photosensor 24 on array 22 corresponds to a location of a single electrode 30 (e.g., each photosensor is located above a corresponding electrode). Typically in such applications, perceived spatial distortion of the image is reduced.

Alternatively, photosensor array 22 and array 88 of electrodes 30 have a different spatial distribution, such that some or all photosensors 24 and electrodes 30 do not have a one-to-one spatial correspondence (e.g., each photosensor is not located above each corresponding electrode). For some such applications, photosensor array 22 maps a signal that is sensed at the center of array 22 to cause stimulation at a radially displaced site on electrode array 88 (i.e., an electrode that is located farther from the center of array 88). For example, device 20 may be configured such that a signal received by photosensors 24 in central portion 26 of array 22 causes driving of an electrode located in outer portion 82 of array 88. Thereby, current is generally not applied to central portion 80 of array 88 (e.g., current is largely not applied to foveola 90). As additionally shown by way of example in FIG. 4A, an electrode located at a first distance D74 from a center of electrode array 88 is configured to apply electrical pulses to the retina in response to a signal from a photosensor in array 22 located at a second distance 76 from a center of photosensor array 22. As shown, first distance D74 is greater than second distance D76.

It is noted that electrodes 30 may be arranged in an array that is square, rectangular, circular, elliptical, or hexagonal, or in other shapes.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising an intraocular device configured to be implanted entirely in a subject's eye, the intraocular device comprising:
   a photosensor array comprising a plurality of photosensors, each photosensor configured to detect ambient photons and to generate a signal in response thereto;
   an arrangement of stimulating electrodes, a spatial density of the electrodes in a central portion of the arrangement being lower than a spatial density of the electrodes in an outer portion of the arrangement, the arrangement being such that: (a) the outer portion surrounds the central portion, and (b) the central portion is large enough to contain therewithin a circle of diameter of at least 100 microns and has a diameter of less than 1000 microns; and
   driving circuitry, coupled to the photosensors, and configured to drive the electrodes to apply electrical pulses to a retina of the eye in response to the signals from the photosensors.

2. The apparatus according to claim 1, wherein the spatial density of the electrodes in the central portion is zero, and wherein the spatial density of the electrodes in the outer portion is at least 4 electrodes per mm^2.

3. The apparatus according to claim 2, wherein the spatial density of the electrodes in the outer portion is between 10 and 100 electrodes per mm^2.

4. The apparatus according to claim 1, wherein the outer portion of the arrangement comprises at least first and second sub-portions, the second sub-portion surrounding the first sub-portion, a spatial density of the electrodes in the second sub-portion of the arrangement being lower than a spatial density of the electrodes in the first sub-portion.

5. The apparatus according to claim 4, wherein the electrodes in the first sub-portion are separated by a distance of 10-100 microns.

6. The apparatus according to claim 4, wherein the electrodes in the second sub-portion are separated by a distance of 300-500 microns.

* * * * *